United States Patent
Takenaka et al.

(10) Patent No.: US 9,291,503 B2
(45) Date of Patent: Mar. 22, 2016

(54) FLOW TYPE SINGLE-PARTICLE SPECTROMETER

(71) Applicant: Hitachi, Ltd., Tokyo (JP)

(72) Inventors: Kei Takenaka, Tokyo (JP); Shigenori Togashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/440,899

(22) PCT Filed: Nov. 8, 2012

(86) PCT No.: PCT/JP2012/078941
§ 371 (c)(1),
(2) Date: May 6, 2015

(87) PCT Pub. No.: WO2014/073064
PCT Pub. Date: May 15, 2014

(65) Prior Publication Data
US 2015/0300881 A1    Oct. 22, 2015

(51) Int. Cl.
*G01N 21/00* (2006.01)
*G01J 3/44* (2006.01)
(Continued)

(52) U.S. Cl.
CPC ............. *G01J 3/4406* (2013.01); *G01J 3/4412* (2013.01); *G01N 15/1434* (2013.01);
(Continued)

(58) Field of Classification Search
CPC ... H01J 37/32935; G01N 21/64; G01N 21/68; G01N 2015/1037; G01J 3/02
USPC ........................................................ 356/72
See application file for complete search history.

(56) References Cited

U.S. PATENT DOCUMENTS

| 5,491,344 A * | 2/1996 | Kenny et al. ............... G01J 3/14 250/459.1 |
| 2006/0103840 A1 | 5/2006 | Fritz et al. |
| 2014/0198313 A1* | 7/2014 | Tracy .................... G01J 3/0291 356/300 |

FOREIGN PATENT DOCUMENTS

| JP | 4-65654 A | 3/1992 |
| JP | 2008-521006 A | 6/2008 |
| JP | 2009-270990 A | 11/2009 |

(Continued)

OTHER PUBLICATIONS

Dragan Isailovic et al., High-Throughput Single-Cell Fluorescence Spectroscopy, Applied Spectroscopy, 2005, pp. 221-226, vol. 59, No. 2.

(Continued)

*Primary Examiner* — Tarifur Chowdhury
*Assistant Examiner* — MD Rahman
(74) *Attorney, Agent, or Firm* — Mattingly & Malur, P.C.

(57) ABSTRACT

A flow type single-particle spectrometer includes a sample container which holds a sample liquid containing a particle to be inspected; a detection channel which is a flow path for optically detecting the particle to be inspected; a waste liquid container which stores the sample liquid flowing out through the detection channel; a liquid feed member; a white light source which emits white light; an excitation light dispersion element which spatially disperses the white light into wavelength components; an excitation light collecting element which collects light; a fluorescence light collecting element which collects fluorescence light and side scattered light; a fluorescence light dispersion element which spatially disperses the fluorescence light into wavelength components; a dispersed light collecting element which collects the fluorescence light dispersed by the fluorescence light dispersion element; and a multi-channel light detector which detects intensity of light for each wavelength.

7 Claims, 8 Drawing Sheets

(51) Int. Cl.
*G01N 21/47* (2006.01)
*G01N 21/64* (2006.01)
*G01N 15/14* (2006.01)

(52) U.S. Cl.
CPC ............ *G01N 21/47* (2013.01); *G01N 21/645* (2013.01); *G01N 2021/4707* (2013.01); *G01N 2021/6417* (2013.01); *G01N 2021/6493* (2013.01); *G01N 2201/06113* (2013.01)

(56) References Cited

FOREIGN PATENT DOCUMENTS

JP 2010-181205 A 8/2010

OTHER PUBLICATIONS

Kei Takenaka et al., Rapid Live Bacterial Counter Using Cassette-Type Flow Cytometry, Transactions of the Japan Society of Mechanical Engineers (C Hen), 2011, pp. 401-410, vol. 77, No. 774.

* cited by examiner

FLOW TYPE SINGLE-PARTICLE SPECTROMETER

TECHNICAL FIELD

The present invention relates to a flow type single-particle spectrometer that continuously obtains a fluorescence spectrum of a particle such as each individual microbe in a liquid and identifies a species of microbe or the like.

BACKGROUND ART

Until now, as a means for measuring a particular species of microbe included in a liquid such as drinking water, a cultural method has been used in general. This cultural method is a method of measuring the number of living microbes by applying a suspension liquid of a liquid sample to a culture medium, cultivating living microbes, and measuring the number of colonies made by cultivated microbes. This method also enables measuring and identifying a particular species of microbe by using a culture medium in which only a particular species of microbe can grow proliferously.

However, this cultural method requires a long inspection time to obtain a measurement result, since it takes one day to some days for microbes to make colonies. Besides, because an inspection process including suspension, dilution, application, colony measurement, etc. is manually performed, inspectors are required to have expertise and skill.

So, as a means for identifying a species of microbe rapidly, there is a method that takes advantage of difference in fluorescence spectra of microbes. This method takes advantage of the fact that different species of microbes have different types of substances in different amounts and are stained to different degrees by a fluorescent dye and, thus, different fluorescence spectra are obtained according to the species. Different fluorescence spectra are also obtained by varying the wavelength of an excitation light. By obtaining fluorescence spectra that are expressed using the wavelength of an excitation light as a parameter (hereinafter referred to as two-dimensional fluorescence spectra), it is possible to determine a species of microbe in more detail.

As a means for obtaining fluorescence spectra of microbes, a fluorescence spectrometer is generally used. The fluorescence spectrometer is an apparatus capable of irradiating a liquid contained in a special measurement cell with an excitation light with a particular wavelength and obtaining a spectrum of fluorescence light that is emitted from the liquid. To obtain fluorescence spectra of particles such as microbes, measurements can be taken by suspending these particles in a liquid such as ultrapure water.

An excitation light of the fluorescence spectrometer is a particular wavelength light drawn from light of a white light source through a grating (diffraction grating) and a slit. The wavelength of the excitation light can be varied by changing the position of the grating. Therefore, it is also easy to obtain two-dimensional fluorescence spectra that are taken by varying the wavelength of an excitation light as a parameter.

However, because a fluorescence spectrum that can be obtained by the fluorescence spectrometer is an average of fluorescence lights that are emitted from all the particles in a liquid, it is impossible to obtain a fluorescence spectrum of each individual particle. So, in order to identify a state and species of a single particle, methods of obtaining a spectrum of fluorescence or Raman scattered light that is emitted from a single particle have recently be reported.

A flow site meter based on Raman detection described in Patent Literature 1, which is mentioned below, obtains a spectrum of Raman scattered light by irradiating a particle which is an object of measurement and flows in a flow path with laser light and detecting, with a multi-channel detector, Raman scattered light that is emitted from the particle and dispersed through a dispersion element such as a grating.

A High-Throughput Single-Cell Fluorescence Spectroscopy described in Nonpatent Literature 1, which is mentioned below, obtains a fluorescence spectrum by irradiating a particle which is an object of measurement and flows in a flow path with 488 nm argon ion laser and detecting, with an ICCD (Intensified charge-coupling device), fluorescence light that is emitted from the particle and dispersed through a grating.

CITATION LIST

Patent Literature

Patent Literature 1: Japanese Unexamined Patent Application Publication (Translation of PCT Application) No. 2008-521006
Nonpatent Literature 1: Applied Spectroscopy, Vol. 59, No. 2, pp 221-226, (2005)

SUMMARY OF INVENTION

Technical Problem

It is effective to take advantage of difference in fluorescence spectra of microbes to identify a species of microbe rapidly. In so far proposed methods and apparatus which are known from the above related art, it was difficult to satisfy requirements sufficiently due to the influences of the number of microbes included in a liquid, their species, and conditions of the liquid.

For example, in a case where a fluorescence spectrometer is used, it is difficult to obtain a fluorescence spectrum unless a sufficient number of microbes (at least $10^7$ per ml) exist in a liquid sample. Because the number of microbes existing in, e.g., tap water is about one per ml or less, it is hard to obtain a fluorescence spectrum unless repeating microbe cultivation and concentration in a sample liquid. If plural microbes are included in a liquid sample, it is hard to identify a species since an obtained fluorescence spectrum is an average of fluorescence spectra of all the microprobes existing there.

With the apparatus proposed in the above Patent Literature 1 and Nonpatent Literature 1, while it is possible to obtain a fluorescence spectrum or a Raman scattered light spectrum using an excitation light with one wavelength fixed, it is hard to obtain a two-dimensional fluorescence spectrum. Therefore, it is hard to identify a microbe among microbes which show similar-form spectra.

Even if a fluorescence spectrometer is used for a detector of the apparatus proposed in the above Patent Literature 1 and Nonpatent Literature 1, it is difficult to obtain a two-dimensional fluorescence spectrum of each individual microbe for the following reason. In a fluorescence spectrometer, the wavelength of an excitation light is set by changing the position of the grating as described previously, and it takes a time of few seconds to change the position. On the other hand, in the flow site meter like the apparatus proposed in the above Patent Literature 1 and Nonpatent Literature 1, a time (measurement time) during which a particle to be measured passes through an area for detection generally falls within a range of few microseconds to milliseconds and, therefore, it is hard to change the wavelength of an excitation light during the measurement time.

The present invention provides a flow type single-particle spectrometer capable of continuously obtaining a fluorescence spectrum of a particle such as each individual microbe in a liquid and identifying a species of microbe or the like.

Solution to Problem

In order to solve the above problem, a flow type single-particle spectrometer of the present invention includes a sample container which holds a sample liquid containing a particle to be inspected; a detection channel which is a flow path for optically detecting the particle to be inspected; an waste liquid container which stores the sample liquid flowing out through the detection channel; a liquid feed member which feeds the sample liquid to the sample container, the detection channel, and the waste liquid container in this order; a white light source which emits white light having a range of wavelengths from an ultraviolet region to a near-infrared region; an excitation light dispersion element which spatially disperses the white light into wavelength components; an excitation light collecting element which collects light dispersed by the excitation light dispersion element into the detection channel; a fluorescence light collecting element which collects fluorescence light and side scattered light emitted from the particle to be inspected; a fluorescence light dispersion element which spatially disperses the fluorescence light collected by the fluorescence light collecting element into wavelength components; a dispersed light collecting element which collects the fluorescence light dispersed by the fluorescence light dispersion element; and a multi-channel light detector which detects intensity of light for each wavelength, the light collected by the dispersed light collecting element.

Advantageous Effects of Invention

According to the present invention, it is possible to obtain a two-dimensional fluorescence spectrum of each individual particle in a liquid. Thus, the present invention provides a flow type single-particle spectrometer which achieves quite a beneficial effect that it is possible to determine a species of particle by utilizing difference in two-dimensional fluorescence spectral forms.

Problems, structures, and advantages other than noted above are clarified by the following description of embodiments.

DESCRIPTION OF EMBODIMENTS

As described previously, it has heretofore been necessary to perform inspection by a cultural method over a few days when identifying a fungus existing in a liquid. However, when contingent fungus generation and interfusion or the like are taken into account, it is required to identify a species of fungus in a liquid in a short period of time from a viewpoint of enhancing safety and sanitation.

The inventors of the present invention examined diverse methods and apparatuses for identifying a species of fungus in a liquid in a short period of time and, in consequence, created the present invention. Preferred embodiments of the invention will be described hereinafter.

It should be noted that, in the present specification, microbes which are included in a liquid and to be detected, are those in a broader scope than ordinary conception of microbes, and what is meant herein is a method and apparatus for inspecting for viruses, bacteria, yeasts, protozoa, fungi, spores, and pollen. Also, in the present specification, for the sake of simplicity of writing, "microbes" not only mean generally defined microbes (bacteria, yeasts, protozoa and fungi) but also mean viruses, spores and pollen.

In the following, embodiments of the present invention will be described with reference to the drawings. It goes without saying that embodiments that will be described later are exemplary and other embodiments can be obtained by combining respective exemplary embodiments together or combining one exemplary embodiment with a publicly or widely known technique or replacement thereof.

First Embodiment

Figure 1:
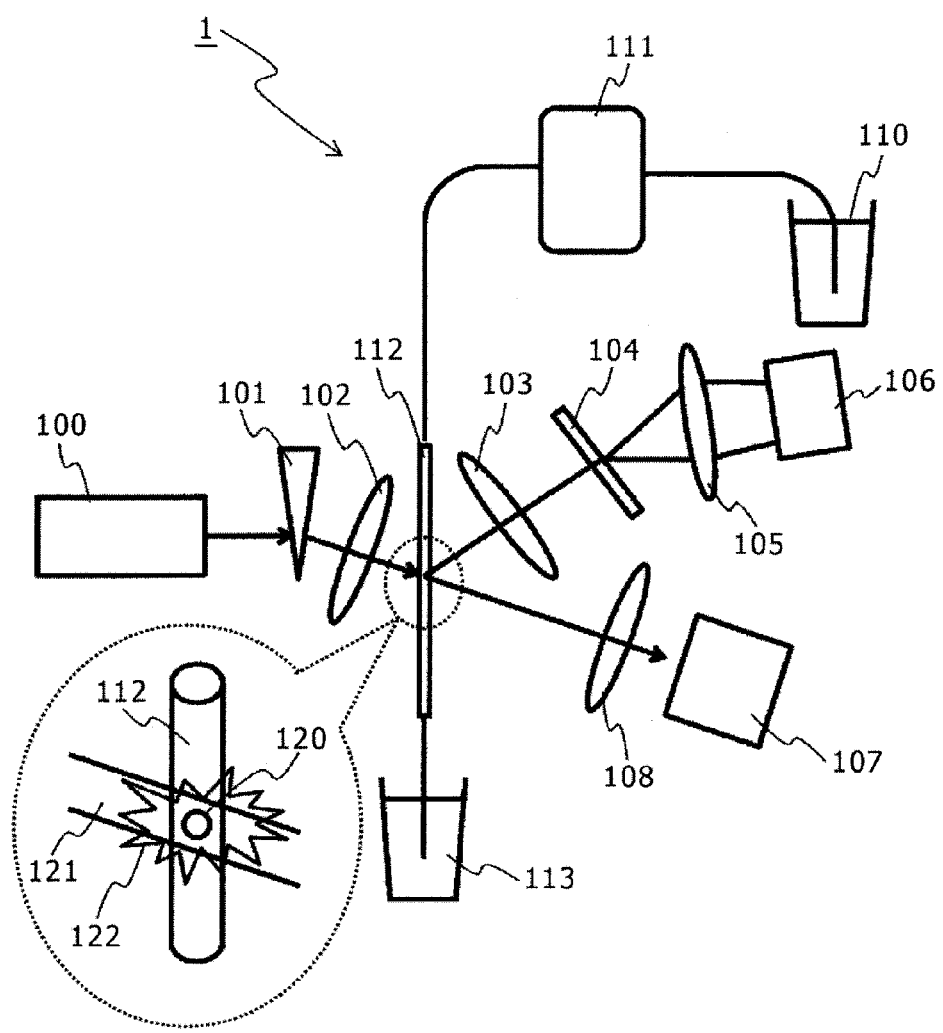
FIG. 1 is an overall schematic structure diagram of a flow type single-particle spectrometer according to a first embodiment of the present invention.

FIG. 1 is an overall schematic structure diagram of a flow type single-particle spectrometer according to a first embodiment of the present invention.

Figure 2:
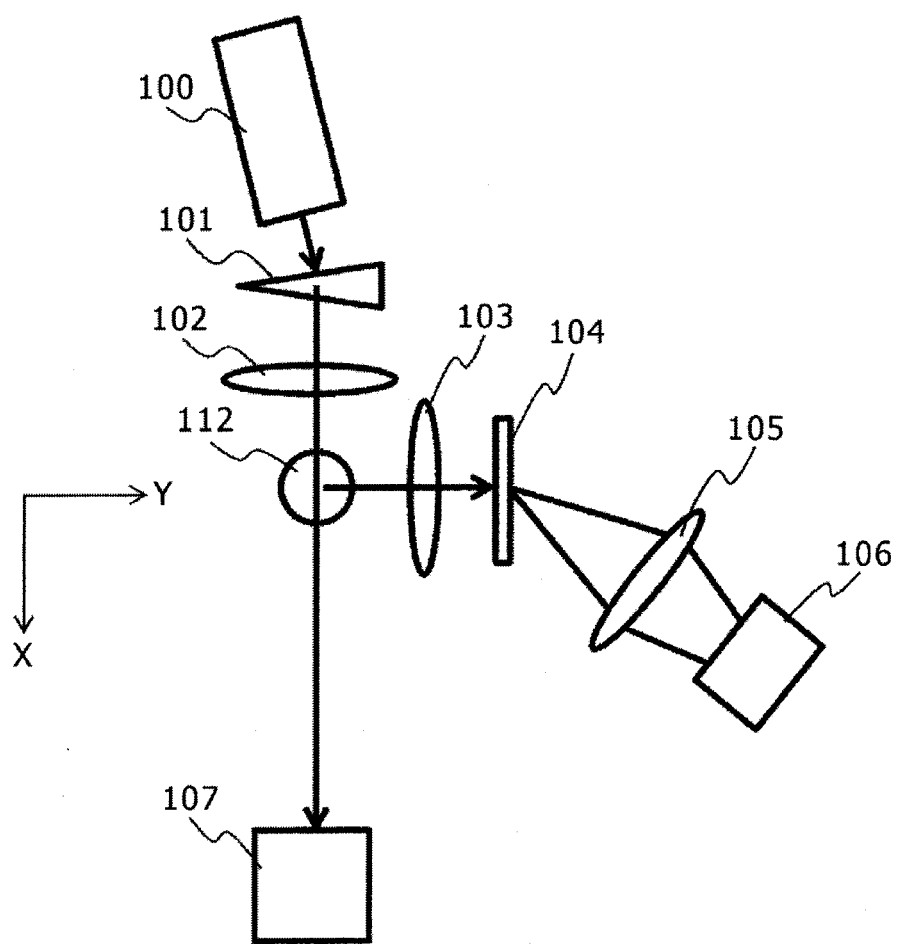
FIG. 2 is a diagram depicting the positional relation of optical system components included in the flow type single-particle spectrometer according to the first embodiment.

FIG. 2 is a diagram depicting the positional relation of optical system components included in the flow type single-particle spectrometer according to the first embodiment.

In FIG. 1, the flow type single-particle spectrometer 1 (which may also be referred to as a single-microbe spectrometer) includes, by rough division, a flow making section for causing a liquid to be inspected (sample liquid) to flow, an optical detection section for optically detecting a microbe included in the liquid, and a control system, not depicted in FIG. 1, which handles control of the flow making section and signals from the optical detection section.

The flow making section includes a sample container 110 which holds a sample liquid, a liquid feed pump 111 for feeding the sample liquid, a detection minute-channel 112 which is a flow path for optically detecting a microbe in the sample liquid while allowing the sample liquid to flow through it, and an waste liquid container 113 for storing the sample liquid that passed through the detection minute-channel 112. A sample liquid in the sample container 110 flows, by the liquid feed pump 111, from the sample container 110 via the detection minute-channel 112 to the waste liquid container 113.

The optical detection section includes a white light source 100 which emits white light, an excitation light dispersion element 101 which is a dispersion element to disperse white light, an excitation light collecting element 102 which is an optical element to collect the dispersed light 121 in the detection minute-channel 112, a fluorescence light collecting element 103 which is an optical element to collect fluorescence light 122 emitted from a microbe 120 flowing in the detection minute-channel 112, a fluorescence light dispersion element 104 which is a dispersion element to disperse fluorescence light collected by the fluorescence light collecting element 103, a dispersed light collecting element 105 which is an optical element to collect the dispersed fluorescence light in a multi-channel light detector 106, the multi-channel light detector 106 which obtains a fluorescence spectrum by detecting the light intensity of the dispersed fluorescence light for each given interval of wavelength, and a forward scattered light collecting element 108 which is an optical element to collect forward scattered light emitted from the microbe 120 flowing in the detection minute-channel 112 into a forward scattered light detector 107.

The following describes details on each of the components mentioned above.

First, the white light source 100 is a light source which emits white light with a wide range of wavelengths from an ultraviolet region to a near-infrared region. As such a light source, a white light laser is preferable because light is easy to collect and a sufficient light intensity is easy to obtain. However, a light source like a halogen lamp or xenon lamp may be used depending on purpose of use.

Next, the excitation light dispersion element 101 and the fluorescence light dispersion element 104 are optical elements to spatially disperse light from the white the light source into wavelength components, and a prism or diffraction grating is used as these elements. Although a prism is used in FIG. 1, a transmissive diffraction grating or reflective diffraction grating may be used.

Next, the excitation light collecting element 102, the fluorescence light collecting element 103, the dispersed light collecting element 105, and the forward scattered light collecting element 108 are optical elements to spatially collect the light incident on the elements, and a lens or curved mirror is used as these elements.

Next, the multi-channel light detector 106 is a light detector capable of detecting the light intensity of light dispersed into wavelength components by the fluorescence light dispersion element 104 and can obtain a spectrum of light incident thereon. What is used as such a detector is a light detector including plural photodiodes and photomultipliers or a light detector including plural light receiving elements such as a CCD (Charge Coupled Device) image sensor, ICCD (Intensified charge Coupling Device) image sensor, or CMOS (Complementary Metal Oxide Semiconductor) image sensor.

Next, the forward scattered light detector 107 is a light detector such as a photodiode or a photomultiplier. As such a detector, a light detector whose sensitivity is lower than the multi-channel light detector 106 is used, since the light intensity of forward scattered light is generally much greater than the light intensity of fluorescence light and side scattered light.

Next, the detection minute-channel 112 is a flow path whose cross section is in a rectangular or circular shape. The dimension of one side or the diameter of the cross section preferably ranges from, e.g., 1 µm to 1 mm and the length preferably ranges from, e.g., 0.01 mm to 10 mm. The larger the dimension of the cross section of the detection minute-channel 112, the smaller pressure loss is. The cross section should be smaller to allow microbes to flow one by one in the path. As the material of the detection minute-channel 112, a light-permeable material is used. Preferably, the material is low in the intrinsic fluorescence because fluorescence is measured, and the optical characteristics such as light permeability, surface accuracy, and refractive index must be excellent. Materials having excellent optical characteristics may be used, such as glass, quartz, polymethacrylic acid methylester, polydimethylsiloxane, cycloolefin polymer, polyethylene terephthalate, and polycarbonate.

Light 121 dispersed by the excitation light dispersion element 101 is delivered to the detection minute-channel 112 by the excitation light collecting element 102. At this time, the wavelength (from an ultraviolet region to a near-infrared region) of the dispersed light 121 varies along the flowing direction of the detection minute-channel 102, and a microbe 120 is irradiated with light having the wavelength varying from an ultraviolet region to a near-infrared region when flowing through the detection minute-channel 112.

Next, the liquid feed pump 111 is a pump to feed the sample liquid to the sample container 110, the detection minute-channel 112, and the waste liquid container 113 in this order and the pulsating flow is preferably smaller. A sheath flow may be used in which a sample liquid flows enclosed by a sheath liquid. In this case, a sheath liquid container for storing the sheath liquid is needed and the liquid feed pump 111 flows the sample liquid and the sheath liquid at the same time. By the use of the sheath flow, the sample liquid is able to flow in the center of the detection minute-channel 112 and the orientation of a microbe in the sample liquid can be coordinated. Thus, more accurate analysis is feasible since the intensity of fluorescence light and scattered light which are emitted from a microbe does not vary depending on the position and orientation of the microbe.

In FIG. 2, the direction of light (x direction in the drawing) emitted from the white light source 100 and passed through the excitation light collecting element is perpendicular to the direction of the detection minute-channel 112 (z direction in the drawing). To minimize the influence of light from the white light source, the fluorescence light collecting element 103 is placed in the y direction in the drawing from the detection minute-channel 112.

Then, descriptions are provided about a procedure for obtaining a two-dimensional fluorescence spectrum of each individual microbe and identifying a microbe through the use of the single-microbe spectrometer 1.

(1) Preprocessing of a Sample Liquid

Appropriate preprocessing is performed on a sample liquid to be inspected. Preprocessing herein involves purification which is a work of removing unwanted substances from a sample liquid and increasing the degree of purity of a microbe to be inspected, condensation which is a work of increasing the concentration of a microbe to be inspected, staining which combines a particular fluorescent substance with a microbe to be inspected, and other works.

(2) Measurement on the Sample Liquid

The sample liquid which has been preprocessed is put into the sample container 110 and the single-microbe spectrometer 1 is activated via the control system. The single-microbe spectrometer 1 feeds the sample liquid to the detection minute-channel 112. Because the wavelength of the light delivered to the detection minute-channel 112 varies from a near-infrared region to an ultraviolet region along the flowing direction of the flow path, a microbe 120 emits fluorescence light which is an excitation light with the wavelength varying from a near-infrared region to an ultraviolet region when the microbe 120 passes through the dispersed light 121.

Figure 3:
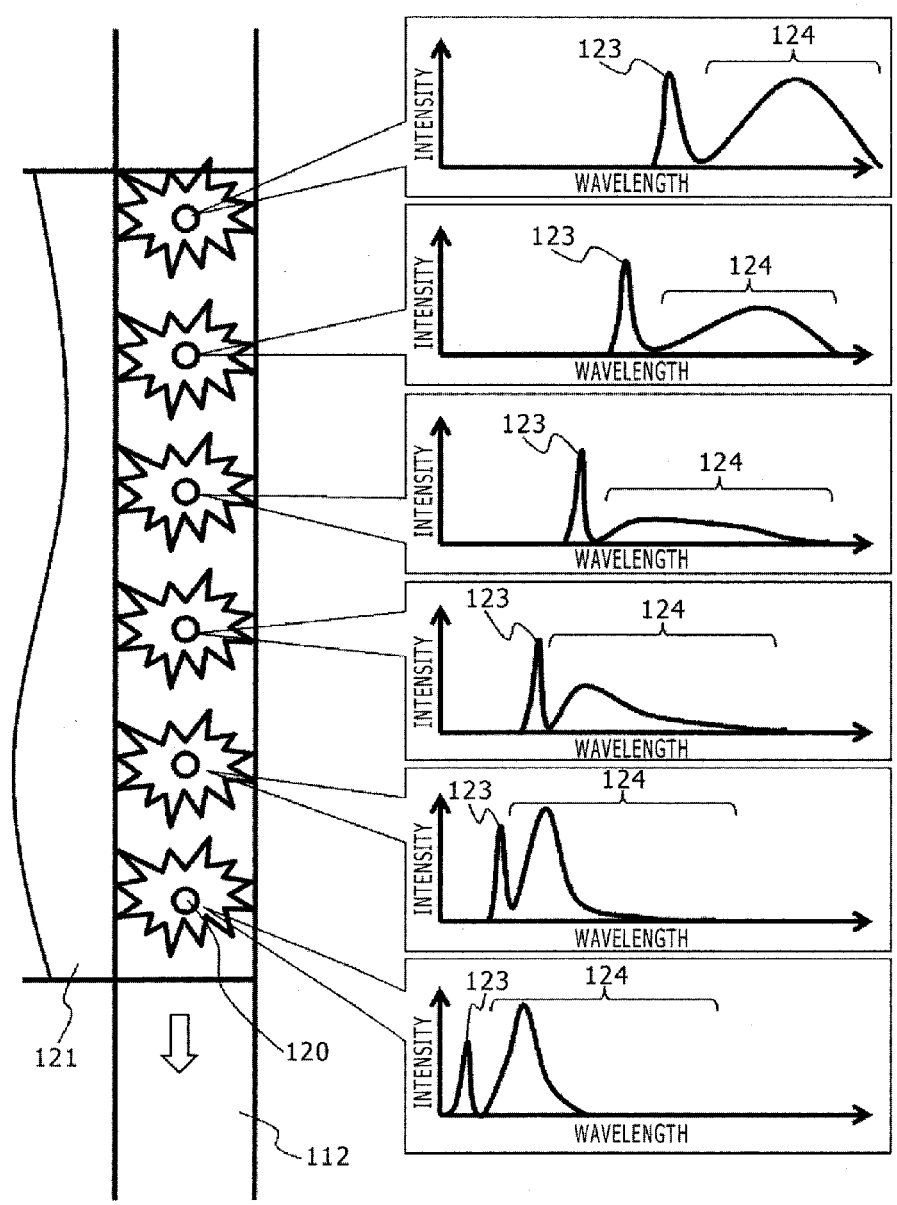
FIG. 3 is a diagram depicting particle positions and fluorescence spectra in the flow type single-particle spectrometer according to the first embodiment.

FIG. 3 is a diagram depicting particle positions and fluorescence spectra in the single-particle spectrometer according to the first embodiment. This drawing depicts the fluorescence spectra that are obtained when the microbe 120 flowing in the detection minute-channel 112 passed through the dispersed light 121.

In FIG. 3, the microbe 120 flows from up to down in the drawing and the wavelength of the dispersed light 121 becomes shorter from top to bottom. The flow direction and the wavelength order may be inverted. Graphs in a right-hand part of the drawing represent the spectra of light emitted from the microbe 120 in its positions, and these spectra are obtained by the multi-channel light detector 106. Light incident on the multi-channel light detector 106 includes side scattered light from the microbe 120 (light scattered sideways with respect to the incident direction of light among the excitation light scattered by the microbe 120) in addition to fluorescence light emitted from the microbe 120.

An obtained spectrum is a superposition of a spectrum of fluorescence light and a spectrum of side scattered light. The wavelength of fluorescence light is longer than that of the excitation light, and the wavelength of scattered light is equal to that of the excitation light. Hence, of two spectrum peaks, a peak 123 appearing at lower wavelength is a spectrum peak of side scattered light and a peak 124 appearing at longer wavelength is a spectrum peak of fluorescence light. When a microbe 120 flows from up to down in the detection minute-channel 112, the wavelength of the excitation light delivered thereto varies from a near-infrared region to an ultraviolet region. Accordingly, an obtained spectrum shifts from longer wavelength to shorter wavelength.

Figure 4:
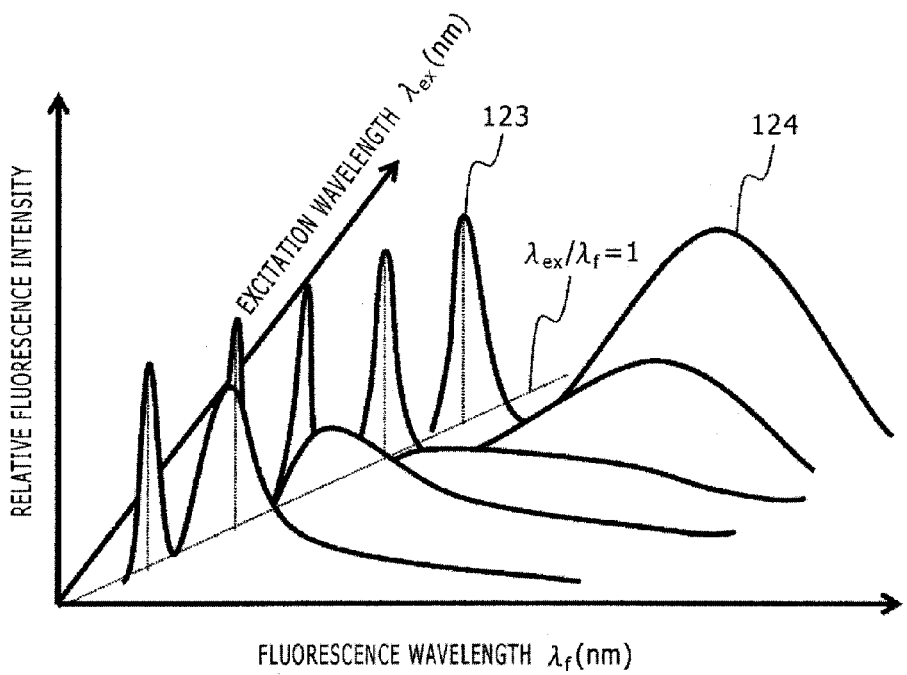
FIG. 4 is a diagram representing a two-dimensional fluorescence spectrum obtained by the flow type single-particle spectrometer according to the first embodiment.

FIG. 4 is a diagram representing a two-dimensional fluorescence spectrum obtained by the single-particle spectrometer according to the first embodiment. This drawing shows a two-dimensional spectrum of fluorescence wavelength $\lambda_f$ and excitation wavelength $\lambda_{ex}$, to which the obtained spectra are transformed.

In FIG. 4, the values of wavelength $\lambda_{ex}$ of the excitation light are considered to be equal to the wavelengths of the peaks of scattered light spectra 123.

(3) Identifying a Microbe

Figure 5:
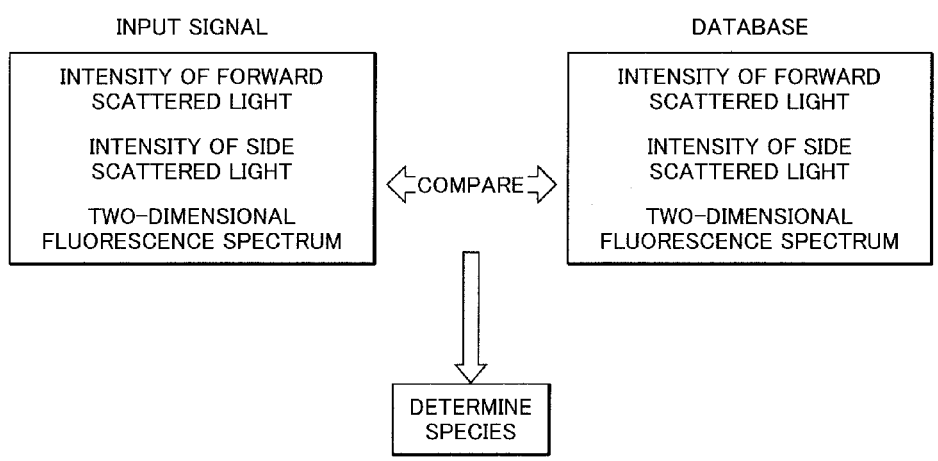
FIG. 5 is a diagram illustrating a way of identifying a species of particle using a two-dimensional fluorescence spectrum obtained by the single-particle spectrometer according to the first embodiment.

The single-microbe spectrometer 1 obtains the intensity of forward scattered light from a microbe 120, the intensity of side scattered light from the microbe 120, and a two-dimensional fluorescence spectrum of the microbe 120. The intensity of forward scattered light indicates the size of the microbe 120. The intensity of side scattered light indicates the complexity of the internal structure of the microbe 120. The two-dimensional spectrum indicates the ease for the microbe to be stained with an autofluorescent substance (such as NADH (Nicotinamide Adenine Dinucleotide)) intrinsic to the microbe and a fluorescent substance introduced in the preprocessing. These attributes differ by species of microbe, and therefore, by quantifying such attributes per microbe in database form, it is possible to identify a species of microbe by comparing the intensity of forward scattered light, the intensity of side scattered light, and the form of the two-dimensional fluorescence spectrum, which have been obtained, with the data in the database (FIG. 5).

Because data on these attributes that is obtained by the present apparatus is data about a single microbe, it is possible to identify each individual microbe even if an impurity that emits fluorescence and other microbes exist in the sample liquid.

Figure 6:
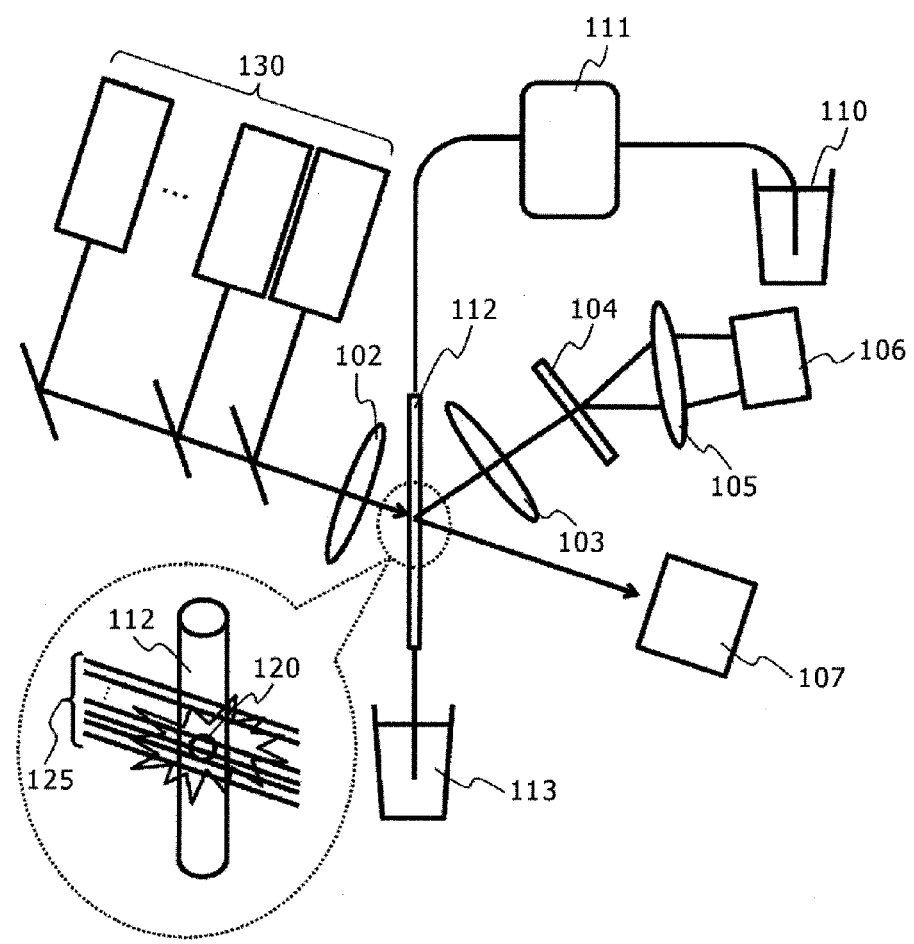
FIG. 6 is an overall schematic structure diagram of the flow type single-particle spectrometer according to the first embodiment.

FIG. 6 is an overall schematic structure diagram of the single-particle spectrometer according to the first embodiment.

In the foregoing embodiment, white light is dispersed by the excitation light dispersion element 101 and the dispersed light is used. A group of single-color light sources 130 may be used in which plural light sources that emit lights of different wavelengths are arrayed, as depicted in FIG. 6. The lights emitted from the group of single-color light sources 130 are delivered to the detection minute-channel 112 in such away that they do not overlap with one another. When a microbe 120 passes through the irradiation areas of the lights 125 from the group of single-color light sources, the microbe 120 emits fluorescence light depending on each excitation wavelength. Thus, it is possible to obtain a two-dimensional fluorescence spectrum in the same way as in the foregoing embodiment.

Second Embodiment

In the foregoing embodiment, preprocessing of a sample liquid was assumed to be performed manually by inspection personnel. The preprocessing is a work that requires a complicated and specialized skill, and difference in inspection personnel's skill and working time may lead to different results of inspection. The following describes an embodiment in which these problems have been solved by automating even the preprocessing process.

Figure 7:
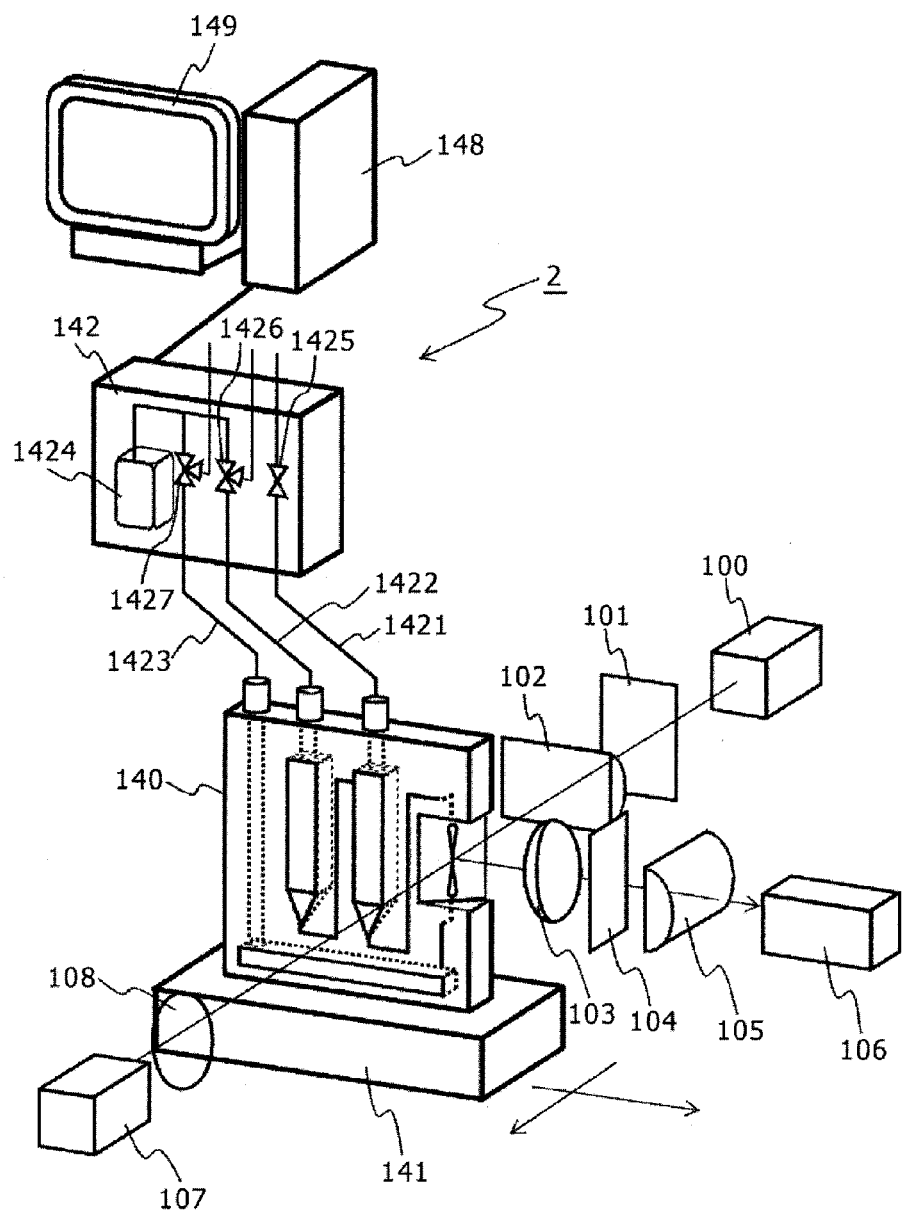
FIG. 7 is an overall schematic structure diagram of a flow type single-particle spectrometer according to a second embodiment of the present invention.

FIG. 7 is an overall schematic structure diagram of a single-particle spectrometer according to a second embodiment of the present invention.

In FIG. 7, a single-microbe spectroscopy system 2 includes a microbe inspection cartridge 140 which internally holds a sample liquid and a reagent and is internally equipped with a mechanism for executing the processes necessary for obtaining a fluorescence spectrum of each individual microbe, a liquid feed control unit 142 for controlling the transportation of a sample liquid and a reagent inside the microbe inspection cartridge 140 via cartridge connecting pipes 1421 to 1423 connected to the microbe inspection cartridge 140 in order to execute the processes necessary for measurements on a microbe, a cartridge support platform 141 which supports the microbe inspection cartridge 140 and adjusts the position of the microbe inspection cartridge 140, and an optical detection section which irradiates a microbe inside the microbe inspection cartridge 140 with dispersed light and detects fluorescence light and scattered light which are emitted from the microbe.

A system device 148 connected to the single-microbe spectroscopy system 2 outputs a control signal to the liquid feed control unit 142 and performs signal processing on electric signals which are input from the optical detection section. A result of measurement obtained by electric signal processing is displayed on an output device 149 connected to the system device 18.

The liquid feed control unit 142 includes a pump 1424. The pump 1424 and aero ports 1451 to 1453 (FIG. 8) of the microbe inspection cartridge 140 are connected to each other by the cartridge connecting pipes 1421 to 1423. The cartridge connecting pipes 1421 to 1423 are fitted with valves 1425 to 1427, respectively. By opening and closing the valves 1425 to 1427, gas with a certain pressure is supplied to the container of the microbe inspection cartridge 140 or the container of the microbe inspection cartridge 140 is opened to air. By this control of the pressure, a sample liquid and a reagent inside the microbe inspection cartridge 140 are transported.

As is the case for the foregoing embodiment, the optical detection section includes a white light source 100 which emits white light, an excitation light dispersion element 101 which is a dispersion element to disperse white light, an excitation light collecting element 102 which is an optical element to collect the dispersed light 121 in the detection minute-channel 112, a fluorescence light collecting element 103 which is an optical element to collect fluorescence light emitted from a microbe 120 flowing in the detection minute-channel 112, a fluorescence light dispersion element 104 which is a dispersion element to disperse fluorescence light collected by the fluorescence light collecting element 103, a dispersed light collecting element 105 which is an optical element to collect the dispersed fluorescence light in a multi-channel light detector 106, the multi-channel light detector 106 which obtains a fluorescence spectrum by detecting the light intensity of the dispersed fluorescence light for each given interval of wavelength, and a forward scattered light collecting element 108 which is an optical element to collect forward scattered light emitted from the microbe 120 flowing in the detection minute-channel 112 into a forward scattered light detector 107.

The excitation light collecting element 102, the fluorescence light collecting element 103, and the forward scattered light collecting element 108 are arranged so that their focal points coincide with each other and configured to enable adjusting the detection minute-channel 144 to a focal position when measurement is performed.

Figure 8:
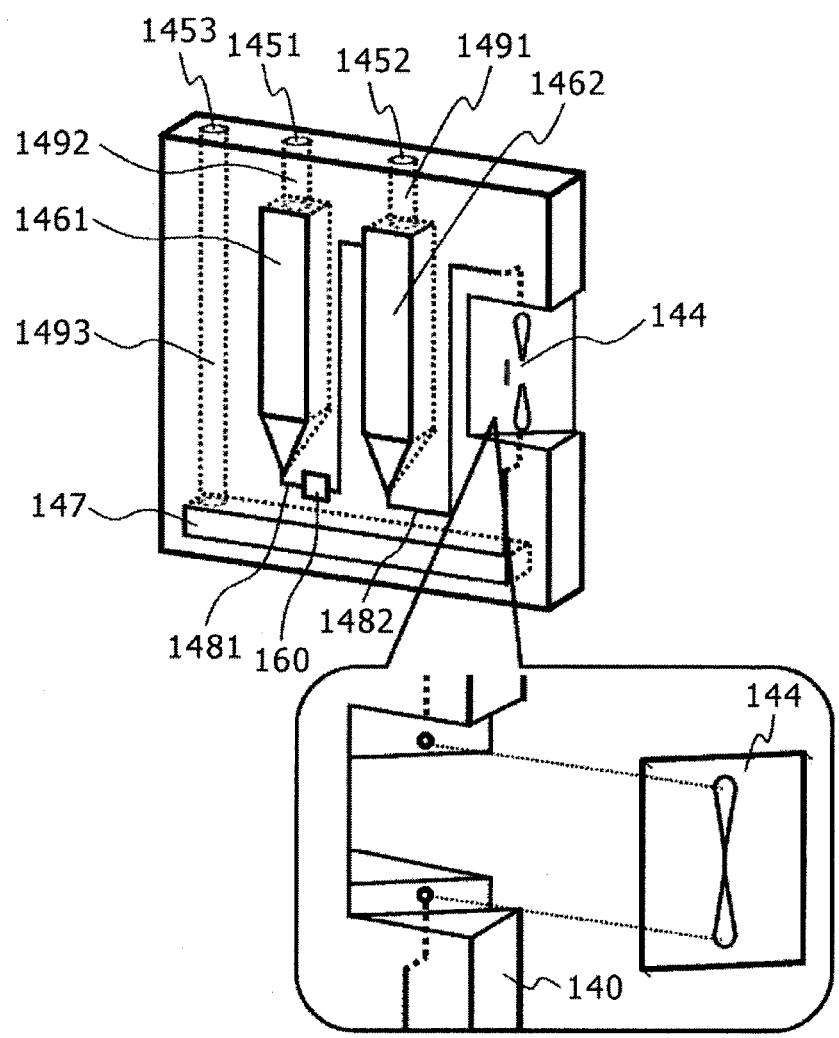
FIG. 8 is a structure diagram of a cartridge included in the flow type single-particle spectrometer according to the second embodiment.

FIG. 8 is a structure diagram of the cartridge included in the single-particle spectrometer according to the second embodiment.

In FIG. 8, the microbe inspection cartridge 140 includes a sample container 1461 for holding a sample liquid, a staining fluid container 1462 which holds a staining fluid (reagent solution) for staining a microbe in the sample liquid and mixes the sample liquid and the staining fluid to react them with each other, a detection minute-channel 144 for irradiating a microbe with an excitation light and observing the microbe, an waste liquid container 147 for discarding a mixed liquid of the sample liquid and the staining fluid which passed through the detection minute-channel 144, solution flow paths 1481 to 1482 for connecting the sample container 1461, the staining fluid container 1462, and the detection minute-channel 144 and allowing the sample liquid and the mixed liquid to flow therein, and aero flow paths 1491 to 1493 connecting the liquid feed control unit 142 and each container to cause the sample liquid and the mixed liquid to flow by air pressure. In the present specification, it is defined that, along the flow of the sample liquid, the sample container 1461 is located upstream and the detection minute-channel 144 is located downstream.

Figure 9A:
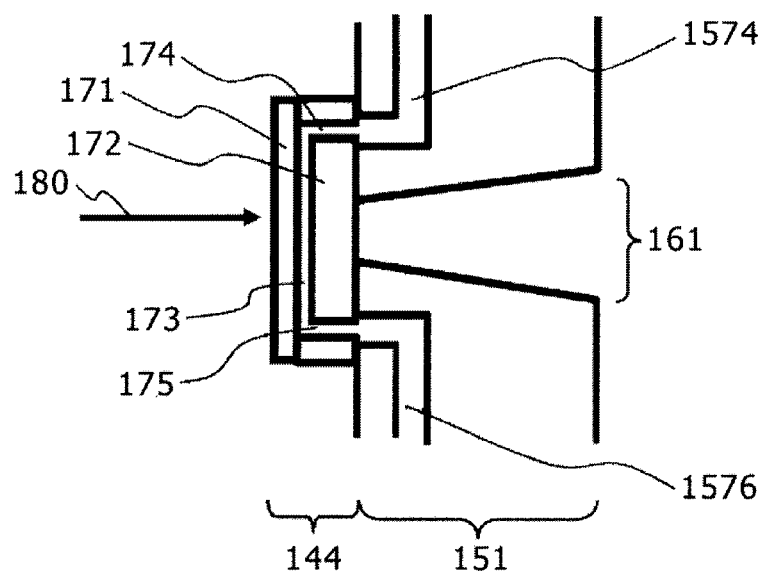
FIG. 9A is a cross-sectional diagram including a detection channel in the cartridge according to the second embodiment.
Figure 9B:
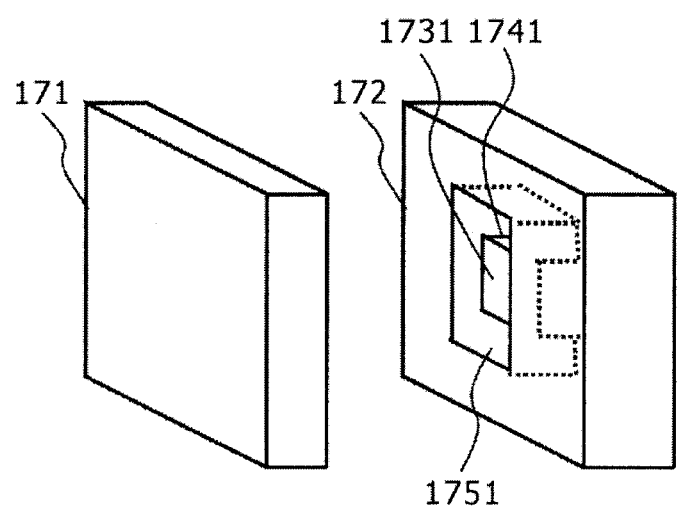
FIG. 9B is a diagram depicting an example of disassembled structure including the detection channel in the cartridge according to the second embodiment.

Using FIGS. 9A and 9B, descriptions are provided for the structure of the detection minute-channel 144 in the microbe inspection cartridge 140.

FIG. 9A is a cross-sectional diagram including the detection channel in the cartridge according to the second embodiment.

FIG. 9B is a diagram depicting an example of disassembled structure including the detection channel in the cartridge according to the second embodiment.

FIG. 9A depicts a joint section where the body 151 and the detection minute-channel 144 are joined together in the microbe inspection cartridge 140. FIG. 9B depicts an exploded perspective view of the detection minute-channel 144.

The cartridge body 151 and the detection minute-channel 144 are manufactured through different processes and joined together. A manufacturing method of the detection minute-channel 144 is described.

In FIGS. 9A and 9B, a microbe detection section 17 includes a cover member 171 and a flow path member 172 and both are made from a thin flat plate. A gully 1731 is formed in the flow path member 172, and through holes 1741, 1751 are formed on both sides of the gully 1731. The cover member 171 and the flow path member 172 are jointed together such that a face where the gully 1731 is formed is a joint face. The detection minute-channel 144 is formed by jointing them. The through holes 1741, 1751 of the flow path member 172 define an inlet 174 of the detection minute-channel and an outlet 175 of the detection minute-channel.

A flow path 1574 formed in the body 151 from the staining fluid container to the detection minute-channel changes the flow path direction at its lower end and forms an opening in the surface of the body 151. Likewise, a flow path 1576 from the detection minute-channel to the waste liquid container changes the flow path direction at its upper end and forms an opening in the surface of the body 151. The opening of the flow path 1574 from the staining fluid container to the detection minute-channel is connected to the inlet 174 of the detection minute-channel, and the opening of the flow path 1576 from the detection minute-channel to the waste liquid container is connected to the outlet 175 of the detection minute-channel.

A window frame 161 for detection is formed in the body 15. The window frame 161 for detection is a through hole or through trench. The window frame 161 for detection is formed between the opening of the flow path 1574 from the staining fluid container to the detection minute-channel and the opening of the flow path 1576 from the detection minute-channel to the waste liquid container. The detection minute-channel 144 which has been manufactured is installed in the body 151, as described previously. As depicted in FIG. 9A, the detection minute-channel 144 is disposed onto the window frame 161 for detection in the body 151.

In the case of the embodiment, the window frame 161 for detection which is a through hole or through trench in the body 151 is provided in back of the detection minute-channel 144. Therefore, the excitation light 180 is only delivered to the detection minute-channel 144 but is not delivered to the body 151. So, reflection light and intrinsic fluorescence light from the body 151 do not take place which cause an increase in background light. To ensure that the excitation light 180 passed through the detection minute-channel 144 is not delivered to the body 151, the cross section of the through hole defining the window frame 161 for detection preferably increases along the radiation direction of the excitation light 180.

The thickness of the cover member 171 ranges from, e.g., 0.01 μm to 1 mm. The thickness of the flow path member 172 ranges from, e.g., 0.01 μm to 1 mm. The cross-section of the detection minute-channel 144 is, e.g., in a square shape, rectangular shape, or trapezoidal shape. The cross-sectional dimension of the detection minute-channel 144 is preferably smaller to allow microbes to flow one by one, though the pressure loss decreases as the cross-sectional dimension increases. The dimension of one side of the cross section of the detection minute-channel 144 preferably ranges from, e.g., 1 μm to 1 mm and the length thereof preferably ranges from, e.g., 0.01 mm to 10 mm. The optical axis of the excitation light 180 which is delivered to the detection minute-channel 144 is perpendicular to the directional vector of the detection minute-channel 144.

Identifying a species of each individual fungus using the microbe inspection cartridge 140 is started in a state in which the microbe inspection cartridge 140 is set in the single-microbe spectroscopy system 2, as depicted in FIG. 7. This measurement process includes a positioning process for positioning the microbe inspection cartridge 140, a preprocessing process for removing foreign substances from a sample liquid and staining a microbe in the sample liquid, and a measuring process for actually measuring a two-dimensional spectrum of the microbe.

The positioning process and the preprocessing process are performed in parallel because they are independent processes, and upon completion of both these processes, the measuring process is performed. The following describes how each liquid or fluid is moved in each process.

In FIG. 8, in the preprocessing process, first, a sample liquid is moved to the sample container 1461. Then, the liquid feed control unit 142 depicted in FIG. 7 applies pressure to the sample container 1461 via an aero port 1451. This increases air pressure inside the sample container 1461. At the same time, the internal pressure of the staining fluid container 1462 is opened to air via an aero port 1491 of the staining fluid container. Because of the pressure difference, the sample liquid enters the staining fluid container 1462 and is mixed with a microbe staining fluid. For mixing, bubbling is used. A fungus in the sample liquid is stained by the staining fluid (a cyanide fluorescent dye is used here).

The water level of the mixed liquid of two liquids does not exceed the highest point of a flow path 1482 from the staining fluid container to the detection minute-channel, the path connecting the staining fluid container 1462 and the detection minute-channel 144. Besides, air enclosed in the staining fluid container 1462 is discharged outside via the aero port 1491 of the staining fluid container. Because the air pressure of the staining fluid container 1462 is equal to the atmospheric pressure, the mixed liquid of two liquids is not forced out to the detection minute-channel 144 and the mixed liquid is allowed to remain in the staining fluid container 1462 for a time necessary for reaction of the mixed liquid.

During the staining, it is desirable to reduce an influence of temperature change on the staining by keeping the temperature of a microbe inspection chip 10 constant.

When the sample liquid flows through a foreign substance removing section 160 to the staining fluid container 1462, foreign substances in the sample liquid are removed from the sample liquid by the foreign substance removing section 160.

The preprocessing process now terminates. In parallel with this preprocessing process, positioning the microbe inspection cartridge 140 is executed.

Upon completion of the above operations, the mixed liquid of the sample liquid and the microbe staining fluid is moved to the detection minute-channel 144. Because dispersed light is delivered to the detection minute-channel 144, as is the case for the foregoing embodiment, a microbe emits fluorescence light depending on each excitation wavelength when the microbe flowing in the detection minute-channel 144 passes through the irradiation area of the dispersed light. Thus, it is possible to obtain a two-dimensional spectrum in the same way as in the foregoing embodiment.

According to the present invention, as described hereinbefore, the apparatus provides a means for accurately identifying a species of each individual particle in a liquid. The apparatus disperses white light, delivers the dispersed light to the detection channel, feeds a liquid including a particle to be measured to the detection channel, and obtains a fluorescence spectrum by dispersing fluorescence light emitted from the particle to be measured. In this way, it is possible to obtain a two-dimensional fluorescence spectrum and to identify a species of particle according to the form of the obtained two-dimensional fluorescence spectrum.

The present invention is not limited to the described embodiments and various modifications are included therein. For example, the foregoing embodiments are those described in detail to explain the present invention clearly and the invention is not necessarily limited to those including all components described. A part of the configuration of an embodiment can be replaced by the configuration of another embodiment. To the configuration of an embodiment, the configuration of another embodiment can be added. As for a part of the configuration of each embodiment, another configuration can be added to it or it can be removed and replaced by another configuration.

LIST OF REFERENCE SIGNS

1 . . . Flow type single-particle spectrometer, 2 . . . Single-microbe spectroscopy system, 18 . . . System device, 10 . . . Microbe inspection chip, 100 . . . White light source, 101 . . . Excitation light dispersion element, 102 . . . Excitation light collecting element, 103 . . . Fluorescence light collecting element, 104 . . . Fluorescence light dispersion element, 105 . . . Dispersed light collecting element, 106 . . . Multi-channel light detector, 107 . . . Forward scattered light detector, 108 . . . Forward scattered light collecting element, 110 . . . Sample container, 111 . . . Liquid feed pump, 112 . . . Detection minute-channel, 113 . . . Waste liquid container, 120 . . . Microbe, 121 . . . Light, 123 . . . Scattered light spectra, 125 . . . Lights, 130 . . . Group of single-color light sources, 140 . . . Microbe inspection cartridge, 141 . . . Cartridge support platform, 142 . . . Liquid feed control unit, 148 . . . System device, 144 . . . Detection minute-channel, 147 . . . Waste liquid container, 149 . . . Output device, 151 . . . Body, 160 . . . Foreign substance removing section, 161 . . . Window frame for detection, 171 . . . Cover member, 172 . . . Flow path member, 174 . . . Inlet of the detection minute-channel, 175 . . . Outlet of the detection minute-channel, 180 . . . Excitation light, 1421 to 1423 . . . Cartridge connecting pipes, 1424 . . . Pump, 1425 to 1427 . . . Valves, 1461 . . . Sample container, 1462 . . . Staining fluid container, 1481 to 1482 . . . Solution flow paths, 1491 to 1493 . . . Aero flow paths, 1731 . . . Gully, 1741 . . . Through hole, 1751 . . . Through hole, 1574 . . . Flow path from the staining fluid container to the detection minute-channel, 1576 . . . Flow path from the detection minute-channel to the waste liquid container

What is claimed is:

1. A flow type single-particle spectrometer comprising:
a sample container which holds a sample liquid containing a particle to be inspected;
a detection channel which is a flow path for optically detecting the particle to be inspected;
an waste liquid container which stores the sample liquid flowing out through the detection channel;
a liquid feed member which feeds the sample liquid to the sample container, the detection channel, and the waste liquid container in this order;
a white light source which emits white light having a range of wavelengths from an ultraviolet region to a near-infrared region;
an excitation light dispersion element which spatially disperses the white light into wavelength components;

an excitation light collecting element which collects light dispersed by the excitation light dispersion element into the detection channel;

a fluorescence light collecting element which collects fluorescence light and side scattered light emitted from the particle to be inspected;

a fluorescence light dispersion element which spatially disperses the fluorescence light collected by the fluorescence light collecting element into wavelength components;

a dispersed light collecting element which collects the fluorescence light dispersed by the fluorescence light dispersion element; and a multi-channel light detector which detects intensity of light for each wavelength, the light collected by the dispersed light collecting element, wherein the spectrometer includes a database having data of an intensity of forward scattered light, an intensity of side scattered light, and the two-dimensional fluorescence spectrum for each species of the particle, and identifies a species of the particle by comparing an intensity of forward scattered light, an intensity of side scattered light, and the two-dimensional fluorescence spectrum of the particle measured by the spectrometer with the data in the database.

2. The flow type single-particle spectrometer according to claim 1, wherein the multi-channel light detector comprises:

a scattered light collecting element which collects forward scattered light emitted from the particle; and a scattered light detector which detects intensity of light collected by the scattered light collecting element.

3. The flow type single-particle spectrometer according to claim 1, wherein the spectrometer judges a peak wavelength appearing at lower wavelength of a spectrum of light obtained by the multi-channel light detector as a wavelength of an excitation light, and obtains a two-dimensional fluorescence spectrum in which the wavelength of the excitation light is a variable.

4. A flow type single-particle spectrometer comprising:

a sample container which holds a sample liquid containing a particle to be inspected;

a detection channel which is a flow path for optically detecting the particle to be inspected;

an waste liquid container which stores the sample liquid flowing out through the detection channel;

a liquid feed member which feeds the sample liquid to the sample container, the detection channel, and the waste liquid container in this order;

a plurality of single-color light sources, each of which emits light having a portion of a range of wavelengths from an ultraviolet region to a near-infrared region;

an excitation light collecting element which collects lights emitted from the plurality of single-color light sources into the detection channel in such a way that the lights do not overlap with one another a fluorescence light collecting element which collects fluorescence light and side scattered light emitted from the particle to be inspected;

a fluorescence light dispersion element which spatially disperses the fluorescence light collected by the fluorescence light collecting element into wavelength components;

a dispersed light collecting element which collects the fluorescence light dispersed by the fluorescence light dispersion element; and a multi-channel light detector which detects intensity of light for each wavelength, the light collected by the dispersed light collecting element, wherein the spectrometer includes a database having data of an intensity of forward scattered light, an intensity of side scattered light, and the two-dimensional fluorescence spectrum for each species of the particle, and identifies a species of the particle by comparing an intensity of forward scattered light, an intensity of side scattered light, and the two-dimensional fluorescence spectrum of the particle measured by the spectrometer with the data in the database.

5. The flow type single-particle spectrometer according to claim 4, wherein the multi-channel light detector comprises:

a scattered light collecting element which collects forward scattered light emitted from the particle; and a scattered light detector which detects intensity of light collected by the scattered light collecting element.

6. The flow type single-particle spectrometer according to claim 4, wherein the spectrometer judges a peak wavelength appearing at lower wavelength of a spectrum of light obtained by the multi-channel light detector as a wavelength of an excitation light, and obtains a two-dimensional fluorescence spectrum in which the wavelength of the excitation light is a variable.

7. A flow type single-particle spectrometer comprising:

an inspection cartridge including:

a sample container which holds a sample liquid containing a particle to be inspected, a reaction container which holds a reagent to react with the particle to be inspected, in which the sample liquid reacts with the reagent, and a detection channel for optically detecting the particle to be inspected flowing through the detection channel;

a pressure supply device which is connected to the inspection cartridge and supplies the sample liquid and the reagent into the inspection cartridge;

a stage which supports the inspection cartridge and moves the inspection cartridge;

a white light source which emits white light having a range of wavelengths from an ultraviolet region to a near-infrared region;

an excitation light dispersion element which spatially disperses the white light into wavelength components;

an excitation light collecting element which collects light dispersed by the excitation light dispersion element into the detection channel;

a scattered light collecting element which collects forward scattered light emitted from the particle;

a scattered light detector which detects intensity of light collected by the scattered light collecting element;

a fluorescence light collecting element which collects fluorescence light and side scattered light emitted from the particle to be inspected;

a fluorescence light dispersion element which spatially disperses the fluorescence light collected by the fluorescence light collecting element into wavelength components;

a dispersed light collecting element which collects the fluorescence light dispersed by the fluorescence light dispersion element; and a multi-channel light detector which detects intensity of light for each wavelength, the light collected by the dispersed light collecting element, wherein the spectrometer includes a database having data of an intensity of forward scattered light, an intensity of side scattered light, and the two-dimensional fluorescence spectrum for each species of the particle, and identifies a species of the particle by comparing an intensity of forward scattered light, an intensity of side scattered light, and the two-dimensional fluorescence spectrum of the particle measured by the spectrometer with the data in the database.

* * * * *